United States Patent [19]

Black et al.

[11] 4,384,476

[45] May 24, 1983

[54] APPARATUS FOR AND METHOD OF ULTRASONICALLY INSPECTING FOODSTUFFS

[75] Inventors: John O. Black, Denville; Frank B. Vanderhoof, Lake Forest; Robert Dederer, Boonton, all of N.J.

[73] Assignee: Metramatic Corp., Landing, N.J.

[21] Appl. No.: 215,251

[22] Filed: Dec. 11, 1980

[51] Int. Cl.³ .............................................. G01N 29/00
[52] U.S. Cl. ..................................................... 73/61 R
[58] Field of Search ............... 73/61 R, 628, 620, 597, 73/599, 625; 426/238, 231

[56] References Cited

U.S. PATENT DOCUMENTS 2,966,056 12/1960 Heller ................................. 73/61 R
3,040,562 6/1962 Fitzgerald et al. ..................... 73/53
3,553,636 1/1971 Baird .................................. 73/61 R
3,667,967 6/1972 Coltart et al. ...................... 426/238
4,208,915 6/1980 Edwards ............................. 73/620

FOREIGN PATENT DOCUMENTS 1018781 2/1966 United Kingdom ............... 73/61 R

Primary Examiner—Stephen A. Kreitman

[57] ABSTRACT

An apparatus and process for detecting the presence of extraneous materials in fluids, e.g., foodstuffs, in which the fluid is passed through a curtain of ultrasonic sound. Reflection or absorption of the ultrasonic sound by extraneous material is detected by ultrasonic sound-receiving means, and an appropriate indication of such detection is given.

15 Claims, 4 Drawing Figures

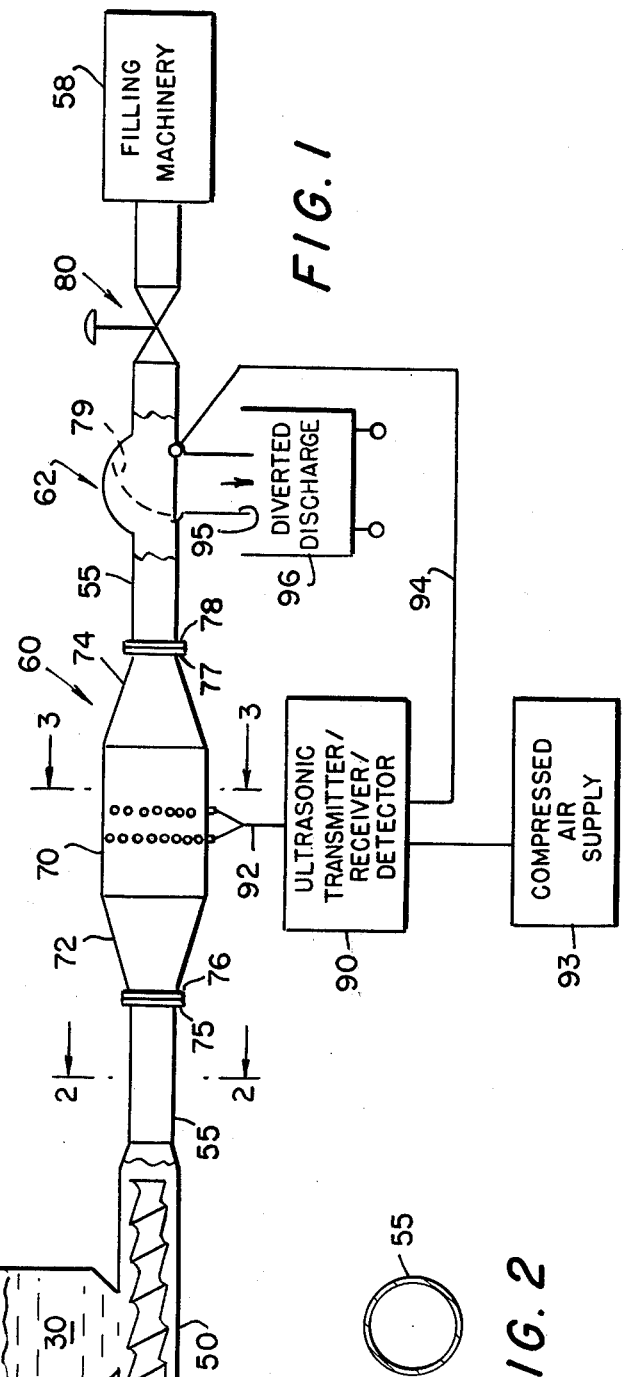
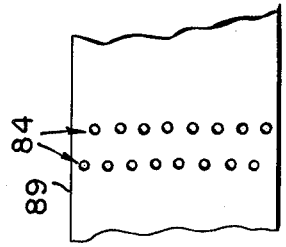
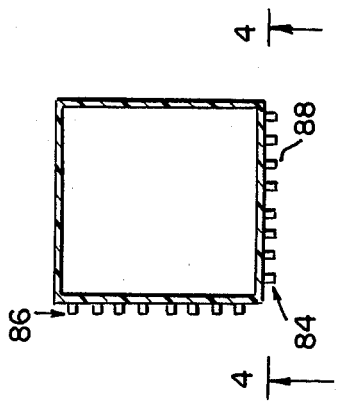
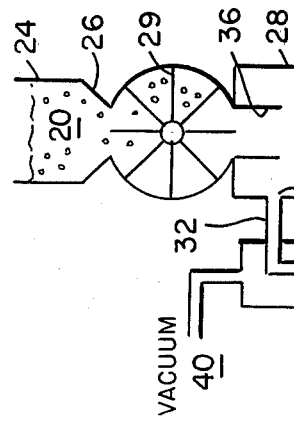

APPARATUS FOR AND METHOD OF ULTRASONICALLY INSPECTING FOODSTUFFS

BACKGROUND OF THE INVENTION

Inspection of fluids such as foodstuffs for the presence of extraneous material has frequently relied upon visual or tactile procedures which limit processing rates and which are subject to operator error and inattention.

Previously, as in U.S. Pat. No. 4,208,915, it has been proposed to compress discrete, solid, form-retaining food products, e.g., frozen hamburgers, against a flexible membrane which can assume the shape of the surface of the solid and transmit thereto, from a transducer, ultrasonic sound which is used for inspection of the solid item in a manner similar to that in which ultrasonic sound has previously been used for inspection of metal parts and castings, welds in metal and the like.

The use of ultrasonic sound energy for examination of the human body for diagnostic procedures in medicine is also known, e.g., "Diagnostic Ultrasonics: Principles and Use of Instruments" by W. N. McDicken, published 1976 by John Wiley & Sons.

However, none of these previously proposed techniques is suitable for the continuous detection of extraneous materials in fluids such as processed foodstuffs.

SUMMARY OF THE INVENTION

In accordance with the present invention, apparatus for detecting the presence, in a flowing fluid, of extraneous material capable of reflecting or absorbing ultrasonic sound energy comprises a conduit adapted to form a passage for fluid to flow in a longitudinal direction therethrough, ultrasonic transducer means associated with said conduit for radiating ultrasonic sound energy throughout an entire cross-section of said flowing fluid in said passage, said cross-section being substantially transverse to said longitudinal direction, and ultrasonic sound-receiving means for receiving said ultrasonic sound radiated throughout said entire cross-section of said flowing fluid, whereby ultrasonic sound reflected or absorbed by said extraneous material in said fluid may be detected to indicate the presence of said extraneous material.

Also in accordance with the present invention is a process for detecting the presence in a fluid of extraneous material capable of reflecting or absorbing ultrasonic sound energy which comprises forming said fluid into a flowable state, flowing said fluid as a flowing stream thereof, radiating ultrasonic sound into said stream transversely to said direction of flow and entirely throughout a transverse cross-section thereof, receiving ultrasonic sound emitted from said transverse cross-section, and detecting ultrasonic sound signals reflected or absorbed by extraneous material in said fluid to indicate the presence thereof.

The apparatus and process of the present invention are highly advantageous in that they may be used with processed fruits and vegetables, soups, processed meats and the like while such are in a fluid condition, e.g., while they are flowing in a closed (or open) pipeline. Thus, flowable pasty or comminuted fruits and vegetables, ketchup, ground meats and the like may be monitored on a continuous basis during processing, and aqueous slurries of fruits and vegetables may be checked for unremoved pits, seeds, stems, or even for rotten cores.

BRIEF DESCRIPTION OF THE DRAWINGS

In the accompanying drawings:

FIG. 1 is a longitudinal view in elevation (partially schematic) of an ultrasonic detection station installed in a conduit for a foodstuff slurry;

FIG. 2 is a sectional view of FIG. 1 taken in the plane 2—2 thereof;

FIG. 3 is a sectional view in elevation of FIG. 1 taken in the plane 3—3 thereof; and FIG. 4 is an enlarged interior view of a portion of the bottom wall illustrated in FIG. 3 illustrating the disposition of ultrasonic transducers thereon.

DESCRIPTION OF THE PREFERRED EMBODIMENT

The following description is to be read in conjunction with the accompanying drawings.

Cooked apple sauce 20 in pumpable, pasty form having water as its continuous liquid phase and containing inclusions of air pockets is charged to a conical hopper 24 at a rate sufficient to keep the throat 26 of hopper 24 covered by the air-containing apple sauce under normal, steady state operating conditions.

The apple sauce 20 is delivered from the hopper 24 to a cylindrical deaeration chamber 28 by a rotary vacuum gate 29. During normal, steady state operation, the deaeration chamber 28 is maintained only partially filled with apple sauce 30, and the chamber is evacuated through a conduit 32 disposed at the top of the chamber 28. The evacuation conduit 32 enters the chamber 28 at an opening 34 near the top thereof, and a depending annular sleeve 36 serves as a shield to prevent splashing or other incidental entry into the conduit or slurry discharged from the rotary gate 29. (The opening 34 and the bottom end of the sleeve 36 are both well above the normal level of slurry in the chamber.) A trap 38 is also provided in the conduit 32 leading to a vacuum source 40.

The deaeration chamber 28 provides a constant source of deaerated apple sauce 30 to a positive displacement screw type pump 50 which pumps the slurry through a closed cylindrical pipeline 55 to filling machinery 58 (indicated schematically).

Disposed in the closed pipeline 55 upstream (toward the pump 50) of the filling machinery 58 is an inspection station 60 at which the pumped deaerated slurry is examined for the presence of foreign or extraneous materials, e.g., pits or pit fragments, by ultrasonic signals. An air-actuated diversion valve 62 is provided in the pipeline between the inspection station 60 and the filling machinery 58.

The inspection station 60 comprises a closed section of light transparent polymeric conduit of polymethylmethacrylate or, preferably, Lexan (4,4 isoprophlidenediphenol polymerized to a molecular weight of about 30,000–35,000). The station 60 consists of a central segment 70 or length of line which is rectangular in cross-section, and two transition segments, 72, 74, one at each end of the rectangular central segment 70, to mate each end of the rectangular central segment to the closed cylindrical pipeline 55 by means of mating flanges 75, 76 and 77, 78.

Inspected, satisfactory apple sauce slurry passes through the diversion valve 62 and is discharged through an exit port 79 for normal discharge into a short length of line 55 leading through a flow control valve 80 to the filling machinery 58, the flow control valve being adjusted to maintain the closed pipeline 55 and inspection station filled with apple sauce slurry under positive pressure at all times during normal processing.

As best illustrated in FIGS. 3 and 4 the central segment 70 of the inspection station 60 consists of a short length of conduit of rectangular (square) shape in which two adjacent walls of one transverse cross section are lined laterally across their outer surfaces with identical transducer arrays 84 and 86. Each array consists of two parallel rows of circular ultrasonic transducers, offset and staggered with respect to the other row. Thus each array provides a series of transducers extending entirely across the complete width of one wall of the central segment to permit each array to sweep the contents of an entire transverse cross section of the central segment 70 with ultrasonic radiation.

Disposition of the arrays 84 and 86 on adjacent walls disposed at right angles to each other insures detection of minute splinters or slivers possibly generating a minimal reflection in one direction, avoids shadowing of particles by gas bubbles, and diminishes any "dead zone" at the transmission sites caused by delays in effecting transition of the crystals and associated electronic circuitry from the transmit mode to the receive mode.

The individual transducers 88 are a ceramic solid solution of lead zirconate and lead titanate and are dimensioned such that they oscillate and amy be driven at a frequency of approximately 2.25 MHz. Each transducer 88 is disposed with its radiating face in contact with the outer surface of the conduit wall 89, and transfer of ultrasonic energy thereto is aided by use of a coupling gel therebetween.

As indicated above, the arrangement of the transducers in two staggered, parallel pulse-echo arrays across the mounting wall 89 from one edge thereof to the other, transverse to the direction of flow of the apple sauce, permits transmission by the crystals, operated in close order sequence or simultaneously in parallel, of a continuous, full and uninterrupted curtain of ultrasonic energy through which all of the apple sauce in the conduit must pass. Use of the pulse-echo arrays facilitates operation primarily based on signal reflections, rather than signal absorbtion, and reduces vulnerability to interference by gas pockets when detection of solid contaminants is desired.

The spacing in the rectangular central segment 70 between the inner face of each of the mounting walls 89 and the inner face of the opposite, parallel wall, determines the maximum length of the normal path the ultrasonic energy must traverse, i.e., must cross and return by reflection. In the preferred embodiment this spacing is three inches, providing a normal signal path for unimpeded signals of six inches.

The transducers 88 are fixed in close order sequence (or alternately simultaneously and in parallel) by ultrasonic energy from an ultrasonic transmitter/receiver/detector 90 delivered through a cable 92. A pulse repetition frequency of 300 pulses/second is employed, and relected ultrasonic signals are received by the transducers and transmitted back to the transmitter/receiver/detector (by the same cable 92). Circuitry in the receiver/detector determines an appropriate delay time for particle transmit and then transmits a pneumatic actuating command signal from a source of pneumatic pressure 93 through a line 94 to the pneumatically actuated diversion valve 62 whenever an abnormal signal is delivered to the detector by the receiver, e.g., an extraneous reflection or absorption. (A visual and/or audible indication of the reception of an abnormal signal may also be presented on a cathode ray tube or buzzer respectively.)

The apple sauce slurry flows through the inspection station under pressure and under conditions of streamline flow. As indicated above, the diversion valve 62 is opened by a command from the detector before it is reached by a flow front which has been the source of an abnormal reflected signal to the inspection station, and is held open by the command so as to discharge through a discharge port 95 therein to a receiver 96, a slug of material containing all of the slurry in that front, e.g., for a period 50% longer in duration than the duration of the abnormal signal.

Apple sauce slurry passing through the inspection station and (the unopened) diversion valve in a normal manner without generating an abnormal signal is delivered to the filling machinery from the flow control valve 80 in the conduit.

A variety of cooked and uncooked foods may be inspected in accordance with the present invention, especially those in which water is present as a continuous phase constituting at least about 30% or more by weight thereof. Examples of foods suitable for inspection in accordance with the invention include, interalia, minced or strained baby foods, (e.g. meats, fruits, vegetables, and mixtures thereof), baloney, sausage fillings, liverwurst, frankfurter meat and the like, tomato ketchup, gruel, puddings, and soups. In addition, pitted or sectioned foods such as olives, peaches, prunes, and cherries, in whole or sliced form, suspended in a continuous liquid medium such as water, sugar syrup, or olive oil, may be inspected for the presence of pits, seeds and stems. Similarly, whole fruits and vegetables such as onions and potatoes may be immersed in a continuous liquid transport medium (such as water) and non-intrusively inspected for homogeniety, e.g., for the presence of rotten cores, embedded solids, or other internal abnormalities.

As indicated, it is preferred to couple the signal from the transducer arrays through the wall defining the inspection chamber, and desirably the wall of the inspection chamber is a material presenting a characteristic impedance to the ultrasonic signal such that the wall couples the signal efficiently from the transducer to the foodstuff. Such construction facilitates sanitary maintenance and equipment repair. Alternately, however, the transducers may, if necessary, be mounted in the wall of the inspection chamber in a pressure-tight manner with their signal-radiating faces in direct contact with the flowing foodstuff. Thus, the inspection chamber may, if desired, be fabricated from a wide variety of suitable materials, including the preferred polymers, stainless steel, and the like.

As further indicated, it is preferred to employ a reflective ultrasonic inspection procedure in which the signal-transmitting transducers are also employed to receive the signal reflected from the foodstuffs being examined (and from the opposed parallel signal-reflecting wall of the conduit). Such pulse-echo technique is highly advantageous in avoiding or reducing generation of extraneous signals by gas bubbles. It is possible, however, to use a through transmitted signal technique by stationing receiving transducers on the conduit wall opposite to, and facing towards, the signal-transmitting transducers.

In carrying out the present invention ultrasonic signals having a frequency in the range of 0.5 to 20 MHz may be employed, signals in the range of about 1–5 MHz being preferred. Generally the lower frequencies, e.g., 0.75 Mhz are suited to detection of large objects such as pits unremoved from halved peaches carried in water or sugar syrup, and frequencies in the range of 1 to 3 MHz are useful in detecting splinters, chips, foil, solid fragments, wires, monofilament nylon fishline as small as 0.003" in diameter, and the like. Further the signal pulse repetition rate may suitably be on the order of 50 to 3000 pulses/second, although a repetition rate of from 100 to 2000 pulses/second is preferred.

The area of the cross-section of slurried foodstuff may vary with the continuous flow capacity desired, and is typically on the order of from 1 to 50 square inches. Normally the width of the conduit across which the ultrasonic signal is transmitted is from 0.5 to 10 inches.

Inspection of highly heterogeneous foodstuffs may be implemented electronically. Thus, for example, inspection for unremoved pits in cherries suspended in water, can be facilitated by establishing an appropriate signal response profile for a suspension of properly de-pitted cherries and then electronically comparing such profile with the signal profiles received during operation to determine the acceptability of the foodstuff in process. Plums, olives, pears and other whole and halved fruits may similarly be inspected, and this technique of electronic comparison of signals for rejection of abnormal material may also be used in the detection of rotten fruits and vegetables.

Although most preferably applied to human and animal foodstuffs (including beverages, e.g., milk, alcoholic beverages, and soft drinks), the apparatus and process of the present invention may advantageously be utilized to inspect a wide variety of other substances provided that they are fluid or fluid suspended and are characterized by a continuous liquid medium. Thus, among the various materials which may be inspected are liquid or pasty substances including petroleum products such as gasoline, motor oil, waxes and greases, and various chemicals solvents, liquid household products, and the like.

It is to be understood that the invention herein illustrated and described is to be limited only by the scope of the claims appended hereto and that various changes, modifications and equivalents may be substituted without departing from the true spirit of the invention.

What is claimed is:

1. Apparatus for detecting the presence in a flowing slurried foodstuff, extraneous material capable of reflecting or absorbing ultrasonic sound energy, said apparatus comprises a conduit adapted to form a passage for slurried foodstuff flowing in a longitudinal direction therethrough, ultrasonic transducer means comprising a plurality of ultrasonic transducers which are associated with said passage for radiating ultrasonic sound energy throughout an entire cross-section of said slurried foodstuff in said passage, thereby forming a curtain of ultrasonic sound, said cross-section being substantially transverse to said longitudinal direction, and ultrasonic sound-receiving means comprising a plurality of ultrasonic receivers for receiving said ultrasonic sound radiated throughout said entire cross-section of said slurried foodstuff, whereby ultrasonic sound reflected or absorbed by substantially any of said extraneous material in said foodstuff regardless of the location of said extraneous material within said cross-section will be detected to indicate the presence of said extraneous material.

2. Apparatus as set forth in claim 1 in which said ultrasonic sound-receiving means is said ultrasonic transducer.

3. Apparatus as set forth in claim 1 in which means for deaerating said foodstuff is disposed to supply deaerated foodstuff to said conduit.

4. Apparatus as set forth in claim 1 in which said passage is rectangular in cross section.

5. Apparatus as set forth in claim 4 in which said passage is square in cross section.

6. Apparatus as set forth in claim 5 wherein said plurality of ultrasonic transducers and said plurality of ultrasonic sound receivers are arranged together in two arrays, said two arrays are disposed on two adjacent sides of said transverse cross-section to thereby radiate ultrasonic sound energy throughout the entire cross-section.

7. A process for detecting the presence in a foodstuff of extraneous material capable of reflecting or absorbing ultrasonic sound energy which comprises forming said foodstuff into a flowable slurry, flowing said slurry as a stream thereof, radiating ultrasonic sound by a plurality of ultrasonic transducers into said stream transversely to said direction of flow and entirely throughout a transverse cross-section thereof, receiving ultrasonic sound by a plurality of ultrasonic sound receivers, emitted from said transverse cross-section and detecting ultrasonic sound signals reflected or absorbed by any extraneous material regardless of the location of said extraneous material within said transverse cross-section in said slurried foodstuff to indicate the presence thereof.

8. A process as set forth in claim 7 in which slurry is deaerated prior to radiating ultrasonic sound thereinto.

9. A process as set forth in claim 7 in which said stream is formed into rectangular cross section and is of said rectangular cross section when radiated with ultrasonic sound.

10. A process as set forth in claim 9 in which ultrasonic sound is radiated into said stream from two adjacent sides of said rectangular cross section.

11. A process as set forth in claim 7 in which said foodstuff has a continuous aqueous phase.

12. Apparatus for detecting the presence, in a fluid, of extraneous material capable of reflecting or absorbing ultrasonic sound energy, said apparatus comprises a conduit adapted to form a passage for fluid to flow in a longitudinal direction therethrough, ultrasonic transducer means comprising a plurality of ultrasonic transducers which are associated with said passage for radiating ultrasonic sound energy throughout an entire cross-section of said flowing fluid in said passage, thereby forming a curtain of ultrasonic sound, said cross-section being substantially transverse to said longitudinal direction, and ultrasonic sound-receiving means comprising a plurality of ultrasonic receivers for receiving said ultrasonic sound radiated throughout said entire cross-section of said flowing fluid, whereby ultrasonic sound reflected or absorbed by substantially any of said extraneous material in said fluid regardless of the location of said extraneous material within said cross-section will be detected to indicate the presence of said extraneous material.

13. Apparatus as set forth in claim 12 wherein said plurality of said ultrasonic transducers and said plurality of ultrasonic sound receivers are disposed in parallel rows within each of said two arrays.

14. A process for detecting the presence in a fluid of extraneous materials capable of reflecting or absorbing ultrasonic sound energy which comprises forming said fluid into a flowable state, flowing said fluid as a stream thereof, radiating ultrasonic sound by a plurality of ultrasonic transducers into said stream transversely to said direction of flow and entirely throughout a transverse cross-section thereof, receiving ultrasonic sound by a plurality of ultrasonic sound receivers emitted from said transverse cross-section, and detecting ultrasonic sound signals reflected or absorbed by any extraneous material regardless of the location within said transverse cross-section in said fluid to indicate the presence thereof.

15. Apparatus as set forth in claim 14 wherein said parallel rows of said plurality of ultrasonic transducers and said plurality of ultrasonic sound receivers are staggered and offset with respect to one another so that ultrasonic sound may be radiated throughout said entire cross-section.

* * * * *